US010210678B1

(12) United States Patent
Manzella et al.

(10) Patent No.: US 10,210,678 B1
(45) Date of Patent: *Feb. 19, 2019

(54) COMMUNICATION SYSTEM AND METHOD FOR USING HUMAN TELEMATIC DATA TO PROVIDE A HAZARD ALARM/NOTIFICATION MESSAGE TO A USER IN A DYNAMIC ENVIRONMENT SUCH AS DURING OPERATION OF A VEHICLE

(71) Applicant: ALLSTATE INSURANCE COMPANY, Northbrook, IL (US)

(72) Inventors: Matthew James Manzella, Glen Ellyn, IL (US); Alinawaz Ismaili, Skokie, IL (US)

(73) Assignee: ALLSTATE INSURANCE COMPANY, Northbrook, IL (US)

( * ) Notice: Subject to any disclaimer, the term of this patent is extended or adjusted under 35 U.S.C. 154(b) by 114 days.

This patent is subject to a terminal disclaimer.

(21) Appl. No.: 14/507,802

(22) Filed: Oct. 6, 2014

(51) Int. Cl.
*G08B 21/06* (2006.01)
*G07C 5/08* (2006.01)
*G08B 21/02* (2006.01)
*B60W 40/09* (2012.01)
*G06Q 40/08* (2012.01)

(52) U.S. Cl.
CPC ............ *G07C 5/085* (2013.01); *B60W 40/09* (2013.01); *G06Q 40/08* (2013.01); *G08B 21/02* (2013.01); *G08B 21/06* (2013.01)

(58) Field of Classification Search
CPC .................. G06Q 40/08; B60W 40/09; B60W 2040/0818; B60W 2040/0872; G08B 21/06; G08B 21/02
See application file for complete search history.

(56) References Cited

U.S. PATENT DOCUMENTS

| 7,072,753 | B2* | 7/2006 | Eberle | B60K 28/02 340/438 |
| 9,031,545 | B1* | 5/2015 | Srey | H04W 4/046 340/3.1 |
| 9,081,650 | B1* | 7/2015 | Brinkmann | G07C 5/0808 |
| 9,104,535 | B1* | 8/2015 | Brinkmann | B60W 40/09 |
| 9,147,353 | B1* | 9/2015 | Slusar | G09B 19/167 |
| 2010/0131304 | A1* | 5/2010 | Collopy | G06Q 30/0224 705/4 |
| 2012/0004933 | A1* | 1/2012 | Foladare | G06Q 40/00 705/4 |
| 2012/0036038 | A1* | 2/2012 | Farmer | G06Q 20/102 705/26.7 |

(Continued)

*Primary Examiner* — Andrew W Bee

(57) ABSTRACT

Systems and methods are disclosed herein for providing near real time communication, such as a warning/notification, to a user based on analysis of various user and vehicle telematic data. The system includes a user with a wearable human telematic sensor providing telematic data about the wearer. Also, the system and method includes at least one vehicle telematic sensor configured to provide telematic data about the vehicle and/or surrounding environment. The various telematic data is communicated and processed to provide a notification back to the user such as a potential safety hazard. The safety hazard may be based upon sensed data specific to the user, specific to the vehicle, or combinations thereof.

15 Claims, 7 Drawing Sheets

(56) References Cited

U.S. PATENT DOCUMENTS

| | | | | |
|---|---|---|---|---|
| 2012/0072240 A1* | 3/2012 | Grosso | ............... | G06Q 40/08 |
| | | | | 705/4 |
| 2014/0019167 A1* | 1/2014 | Cheng | ............... | G06Q 40/08 |
| | | | | 705/4 |
| 2014/0167967 A1* | 6/2014 | He | ............... | B60Q 9/00 |
| | | | | 340/576 |
| 2014/0172467 A1* | 6/2014 | He | ............... | B60K 28/066 |
| | | | | 705/4 |
| 2014/0257867 A1* | 9/2014 | Gay | ............... | G07C 5/00 |
| | | | | 705/4 |
| 2014/0277902 A1* | 9/2014 | Koch | ............... | G07C 5/008 |
| | | | | 701/29.1 |
| 2014/0300739 A1* | 10/2014 | Mimar | ............... | H04N 7/188 |
| | | | | 348/148 |
| 2015/0025917 A1* | 1/2015 | Stempora | ............... | G06Q 40/08 |
| | | | | 705/4 |
| 2015/0254955 A1* | 9/2015 | Fields | ............... | G08B 21/02 |
| | | | | 705/4 |

\* cited by examiner

600

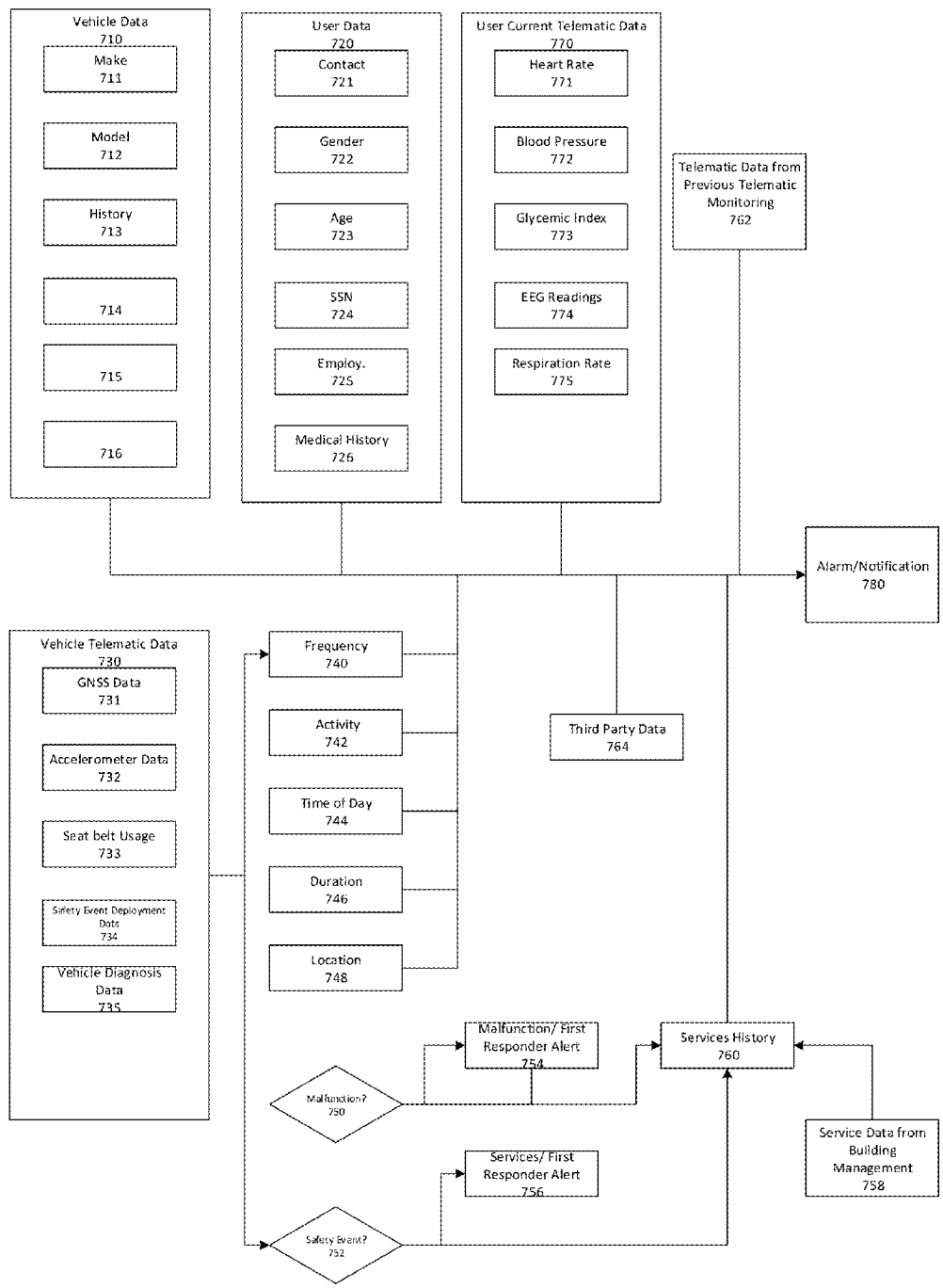

COMMUNICATION SYSTEM AND METHOD FOR USING HUMAN TELEMATIC DATA TO PROVIDE A HAZARD ALARM/NOTIFICATION MESSAGE TO A USER IN A DYNAMIC ENVIRONMENT SUCH AS DURING OPERATION OF A VEHICLE

FIELD OF THE INVENTION

In general, the invention relates to a computerized system and method for providing a personal warning or alarm notification based on human telematic data in or around a dynamic environment such as operating a vehicle.

BACKGROUND

The use of telematics sensors and other location-aware, status-aware devices have begun to make their way into the marketplace. Currently, they are used with vehicles to determine a driver's speed or perhaps location/route traveled. This information is typically used to ensure employees are not deviating from established travel routes or driving in an unsafe fashion. The data received is currently data depicting how or where a person has driven. It is inherently dated or otherwise depicting past events when viewed or analyzed.

As the current systems and methods are not set up to provide real time analysis of an individual or their current environment, the systems cannot provide a user with information regarding a potential hazardous situation they may be near or otherwise affected by.

As such, what is needed is a system and method that monitors a user and their environment that is capable of providing a near real time warning or other notification to the user.

SUMMARY

A system for processing vehicle safety status data and user data related to determination of a hazard alarm/notification for a user. The system includes a communications interface configured to receive health telematics data collected by a telematics data acquisition device. The telematics data acquisition device is configured to collect health telematic data of a vehicle safety status, the health telematic data being indicative of the vehicle safety status health while the user is operating a vehicle. Additionally, the data acquisition device is also configured to receive vehicle telematic data collected by a telematics data acquisition device, wherein the telematics data acquisition device is configured to collect telematics data of a vehicle indicative of vehicle safety. The device provides the health telematic and the vehicle telematic data to a business logic processor for the development of a hazard alarm/notification based on at least one of the received health telematics data or vehicle telematic data. Further, the system transmits the hazard alarm/notification to the user.

A still further aspect includes one or more tangible computer readable media storing computer readable instructions that, when executed, perform a method of providing a hazard alarm/notification to a user based upon human health telematic data and vehicle telematic data. Including receiving health telematic data via a communications interface health telematics data collected by a telematics data acquisition device. Also, receiving vehicle telematic data via a communications interface vehicle telematics data collected by a telematics data acquisition device. This includes determining a hazard alarm/notification based on the received user health telematic data and the received vehicle telematic data. Also included is transmitting the hazard alarm/notification to the user.

Yet another non limiting aspect of this disclosure includes a sensor system that has a first sensor, to be worn by a user. The first sensor outputting a first sensor data indicative of measured at least one user health telematic data. Additionally included is a second sensor, in communication with a vehicle being operated by the user, the second sensor outputting a second sensor data indicative of a measured at least one vehicle telematic data. Also, a computing unit, in communication with the first sensor and the second sensor. The computing unit storing program instructions for execution by the computing unit to, receive the first sensor data and the second sensor data, calculate a risk level associated with the first sensor data and the second sensor data, and, output a hazard alarm/notification feedback signal to the user indicative of the risk level of the first sensor data and the second sensor data.

Another aspect of the disclosure is a method for providing a hazard alarm/notification based upon human user health telematic data and vehicle telematic data. The method comprising, receiving, by a communications interface, user health telematics data collected by a telematics data acquisition device. The user health telematics data being indicative of a user health status health while operating a vehicle. Also, receiving, by a communications interface, vehicle telematic data collected by a telematics data acquisition device, the vehicle telematics data being indicative of a vehicle safety status health while being operated by a user. Further, determining, by the business logic processor, a hazard alarm/notification for the user based on the received user health telematic data and vehicle telematic data. Additionally, providing by the business logic processor the hazard alarm/notification to the communications interface. Also, transmitting, by the communications interface, the hazard alarm/notification to the user.

An additional aspect includes a method of providing a hazard alarm/notification to a user based upon human telematic data and vehicle telematic data. The method includes providing a first sensor to be worn by a user and a first sensor data indicative of measured at least one user health telematic data. Further, the method includes providing a second sensor, in communication with a vehicle being operated by the user, the second sensor outputting a second sensor data indicative of a measured at least one vehicle telematic data. Still further, the method includes providing a computing unit, in communication with the first sensor and the second sensor, the computing unit storing program instructions for execution by the computing unit. The computing unit receives the first sensor data and the second sensor data, calculates a risk level associated with the first sensor data and the second sensor data and, provides an output hazard alarm/notification indicative of the risk level of first sensor data and the second sensor data to the user.

BRIEF DESCRIPTION OF THE DRAWINGS

FIG. 7 is a data flow diagram illustrating a method for using telematics data, vehicle telematic data, user data, user telematic data, and service data, according to an illustrative embodiment of the invention.

DETAILED DESCRIPTION

To provide an overall understanding of the invention, certain illustrative embodiments will now be described, including systems and methods for monitoring individual telematic data, such as, individual health status while simultaneously monitoring vehicle telematic data. This system and method is also used to provide real time feedback to the user based upon the monitored user and vehicle telematic data. Suitable, non-limiting examples of the type of real time feedback provided include alarms or warnings as to potential safety or hazardous conditions. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1:
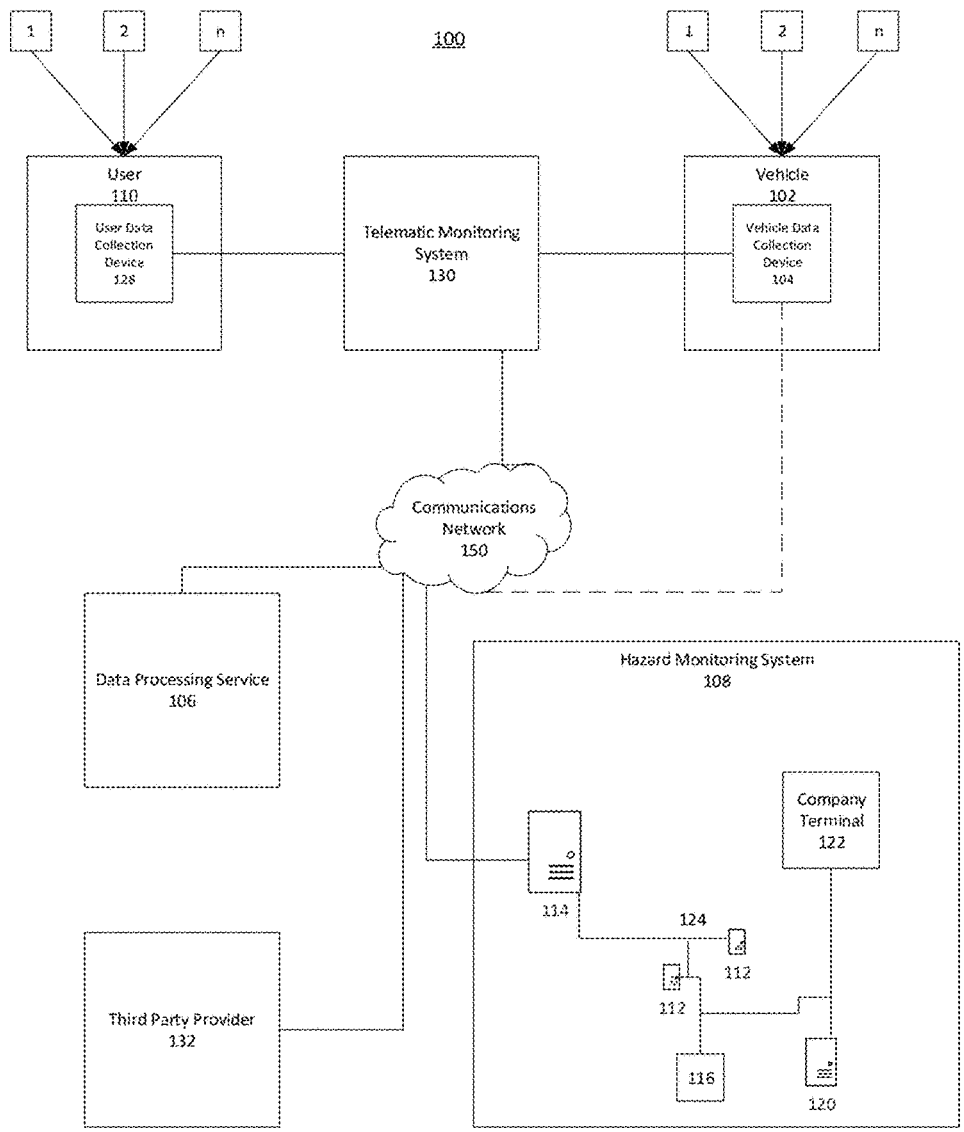
FIG. 1 is an architectural model of a system configured for providing an alarm/notification to a user based upon user telematic data according to an illustrative embodiment of the invention.

FIG. 1 is a block diagram of a system 100 for monitoring individual health status and a vehicle environment status, according to an illustrative embodiment. The system 100 uses telematic data to determine the behavior and safety of a vehicle environment status, and its user/occupier. A monitoring entity uses data related to vehicle speed, vehicle handling, driving times, distance traveled, location of the vehicle, and condition of the vehicle etc., to assess the behavior and safety of the user. Additionally, the monitoring entity uses data related to individual health measurements, and user environmental measurements to further assess the behavior and safety of the user. With a sufficient amount of data, the monitoring entity can calculate a safety status for the user based on user health measurements, user environmental measurements, and the condition of the vehicle/user environment. Based upon the various telematic and other data received, a warning or other user feedback may be provided to the user.

The system includes a user 110 having at least one user data collection device 128 in communication with the user 110. The user data collection device 128 is configured to measure any variety of user health status measurements such as, without limitation body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants, etc. Suitable exemplary sensing equipment includes wearable devices like Nike's Fuelband™ or a similar activity tracking sensor such as Fitbit™. Still further, Netatamu's June™ and Sunsprite™ by GoodLux Technology are suitable non-limiting examples of personal sun exposure detectors. By way of further non-limiting example of a personal sensor is a personal air pollution sensor by Carnegie Mellon under the name Airbot™. Likewise, there are a variety of smart clothing options available that include imbedded sensors for health monitoring. Further, wearable EEG sensors are also known, as are blood glucose level sensors, and transdermal sensors for determination of alcohol consumption. Alternatively or additionally, the user data collection device 128 may be configured to sense environmental factors around the user 110. In this manner, it can be determined if the user 110 has entered or is in an unsafe area. Suitable non-limiting examples of such user data collection device(s) 128 include oxygen sensors, carbon monoxide sensors, methane sensors, pollution sensors, radiation sensors, etc. All such user data collection device(s) 128 are capable of transmitting data via a network or direct wire.

The system 100 also includes one or more vehicles 102, each having a vehicle data collection device 104. For the purposes of this disclosure, a "vehicles 102" is defined as any automobile, motorcycle, truck, bus, watercraft, aircraft, or any other vehicle operated by a driver. A vehicle data collection device 104 is coupled to a vehicle 102 for collecting data about the vehicle's location, movements, or other information that can be used to determine driving behavior and safety. The vehicle data collection device 104 may be positioned inside the vehicle, attached to the outside of the vehicle, or integrated into the vehicle. For vehicles with multiple drivers, the data may be associated with the vehicle itself or with the individual drivers.

In some embodiments, data from the user data collection device 128 and/or vehicle data collection device 104 is directly transmitted to the monitoring entity without traveling through the communications network 150. In other embodiments, the user data collection device 128 and/or vehicle data collection device 104 is in communication with a telematic monitoring system 130 over a communications network 150. The user data collection device 128 and/or vehicle data collection device 104 may communicate with the monitoring entity 130 though a wireless network such as a cellular network or by using a wireless Internet connection.

The user data collection device 128 and/or vehicle data collection device 104 can be any computing device or plurality of computing devices in cooperation having a data collection sensor (e.g., an antenna or a accelerometer), a processor, a memory, and a means for transmitting the collected data. The vehicle 102 or user data collection device 128 and/or vehicle data collection device 104 may include an antenna for receiving signals from global navigation satellite system (GNSS) satellites, numbered 1 through n in FIG. 1. In some embodiments, the user data collection device 128 and/or vehicle data collection device 104 is also configured to process the collected data, e.g., by summarizing and/or compressing the data. In some embodiments, the data processing protects the user's privacy by encrypting the data, removing location information, producing summary information, or taking other measures to reduce the likelihood that location information or other sensitive information are received by third parties. The components of the vehicle data collection device 104 are discussed further in relation to FIG. 3, and an alternative data collection device is described in relation to FIG. 4. Similar structure may be used to form the user data collection device 128.

In some embodiments, rather than sending collected data directly to the user data collection device 128 and/or vehicle data collection device 104 or the telematic monitoring system 130, collected data may be sent directly to a data processing service 106, which processes the data to determine user safety and vehicle safety information. This can help protect a user's privacy, since the telematic monitoring system 130 does not receive detailed data about a user's location, but only receives summary information, e.g., a vehicle or environmental/safety rating or score. Using a data processing service 106 in some implementations is also preferable to having the user data collection device 128 and/or vehicle data collection device 104 process data because it reduces the processing power needed by user data collection device 128 and/or vehicle data collection device 104 and in addition, using a third party data processing service 106 may also make it more difficult to tamper with the data. The data processing service can perform additional monitoring functions, such as vehicle security monitoring or providing location-based alerts (e.g., alerting a parent or employer when a vehicle sensor is activated) and safety alerts. Additionally, or to the contrary, if a potentially dangerous condition is determined, warning messages may be sent to the user 110.

The telematic monitoring system 130 includes a plurality of application servers 112, a plurality of load balancing proxy servers 114, a database 116, a processing unit 120, and company terminal 122. These computing devices are connected by a local area network 124.

The application servers 112 are responsible for interacting with the user data collection device 128 and/or vehicle data collection device 104 and/or the data processing service 106. The data exchange between the telematic monitoring system 130 and user data collection device 128 and/or vehicle data collection device 104, and/or data processing service 106 can utilize push and pull technologies where the application servers 112 of the telematic monitoring system 130 can act as both a server and client for pushing data to the telematic monitoring system 130, user data collection device 128 and/or vehicle data collection device 104, and/or data processing service 106 (e.g., which vehicles to monitor, when to stop data collection, rules for monitoring services requested by the customer) and for pulling data from the telematic monitoring system 130, user data collection device 128 and/or vehicle data collection device 104, and/or data processing service 106. The application servers 112 or other servers of the telematic monitoring system 130 can request to receive periodic data feeds from the telematic monitoring system 130, the user data collection device 128 and/or vehicle data collection device 104, or data processing service 106. The communication between the application servers 112 and the telematic monitoring system 130, user data collection device 128 and/or vehicle data collection device 104, and/or data processing service 106 can follow various known communication protocols, such as TCP/IP. Alternatively, the application servers 112 and telematic monitoring system 130, user data collection device 128 and/or vehicle data collection device 104, and/or data processing service 106 can communicate with each other wirelessly, e.g., via cellular communication. Wi-Fi, Wi-Max, or other wireless communications technologies or combination of wired or wireless channels. The load balancing proxy servers 114 operate to distribute the load among application servers 112.

In an embodiment, the database 116 stores information about specific users. For each user, the database 116 includes for example and without limitation, the following data fields: name, age, height, weight, gender, emergency contact numbers, medical information, geographic information, or derivations thereof.

The processing unit 120 is configured for determining the effect of a hazard event based on user behavior and other information related to the user and the vehicle/vehicle environment. The processing unit 120 may comprise multiple separate processors, such as a user behavior processor, which analyzes user behavior from raw or processed data received from the telematic monitoring system 130, user data collection device 128 and/or vehicle data collection device 104, and/or data processing service 106 over the communications network 150; and a business logic processor, which determines a hazard notification based on, among other things, user health state, user environment state and the user behavior. An exemplary implementation of a computing device for use in the processing unit 120 is discussed in greater detail in relation to FIG. 2.

The user terminals 122 provide various user interfaces to user to interact with the processing system 120. The interfaces include, without limitation, interfaces to review vehicle/vehicle environment data; to review vehicle data; to review customer or potential customer measured health data; to retrieve data related to hazard events; and to manually adjust user behavior ratings. In some instances, different users may be given different access privileges. Such interfaces may be integrated into one or more websites for managing the hazard monitoring system 108 presented by the application servers 112, or they may be integrated into thin or thick software clients or stand alone software. The company terminals 122 can be any computing devices suitable for carrying out the processes described above, including personal computers, laptop computers, tablet computers, smartphones, servers, and other computing devices.

User terminals can provides various user interfaces to customers to interact with the hazard monitoring system 108 over the communications network 150. Customers may also use their personal computers, smartphones, tablet computers, or other computing devices as terminals for accessing user interfaces provided by the hazard monitoring company. For example, customers can access a web page or application provided by the hazard monitoring company to enter information pertaining to changes in their monitoring status or boundaries, e.g., changes in sensor sensitivity, addition or subtraction of users, addition or subtraction of vehicles, relocation, addition or subtraction of various user data collection devices 128, etc.

In some embodiments, the user data collection device 128 and/or vehicle data collection device 104 is not continually connected to the hazard monitoring system 108 via the network 150. For example, the user data collection device 128 and/or vehicle data collection device 104 may be configured to temporarily store data if the user data collection device 128 and/or vehicle data collection device 104 becomes disconnected from the network, like when it travels out of range of cellular towers. When the connection is restored, the user data collection device 128 and/or vehicle data collection device 104 can then transmit the temporarily stored data to the hazard alarm/warning company system 108. The user data collection device 128 and/or vehicle data collection device 104 may alternatively be configured to connect to the communications network 150 through a user's home Wi-Fi network. In this case, the user data collection device 128 and/or vehicle data collection device 104 stores all sensed data until it returns to the vicinity of the user's home, connects to the user's wireless network, and sends the data.

In some embodiments, data from a third party data provider 132 is accessed by one or more of the user data collection device 128 and/or vehicle data collection device 104, the data processing service 106, the hazard monitoring company system 108, and/or the telematic monitoring system 130 over the communications network 150. Data from a third party data provider 132 can be used in calculating a hazard alarm/warning event. For example, the third party data provider 132 can provide geologic/seismic, traffic pattern, traffic blockage, EMS, or weather data that is processed in conjunction with the received telematics data to evaluate user behavior in view of the environmental/vehicle conditions.

Figure 2:
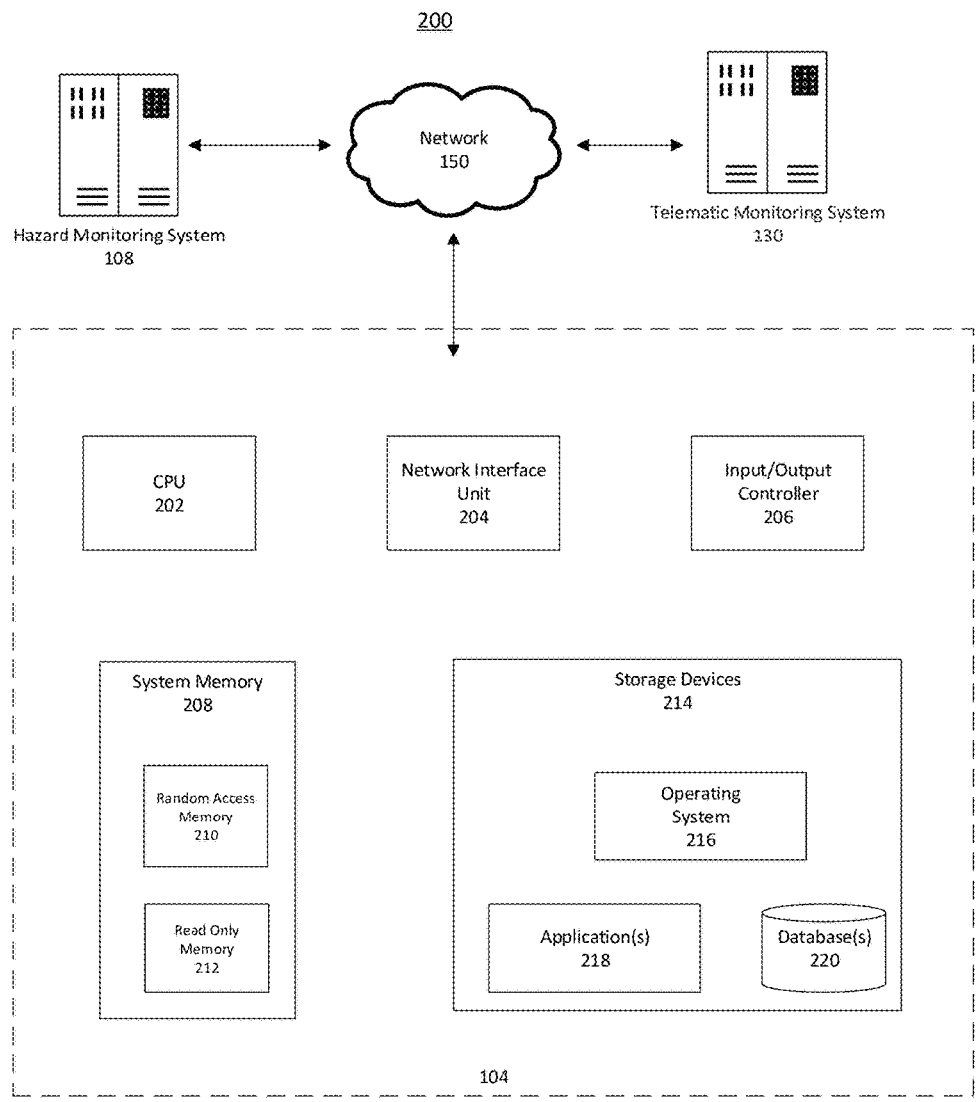
FIG. 2 is a block diagram of a computing system as used in FIG. 1, according to an illustrative embodiment of the invention.

FIG. 2 is a block diagram of a computing device 200 used for carrying out at least one of user health and/or behavior processing and business logic processing described in relation to FIG. 1, according to an illustrative embodiment of the invention. The computing device comprises at least one network interface unit 204, an input/output controller 206, system memory 208, and one or more data storage devices 214. The system memory 208 includes at least one random access memory (RAM) 210 and at least one read-only memory (ROM) 212. All of these elements are in communication with a central processing unit (CPU) 202 to facilitate the operation of the computing device 200. The computing device 200 may be configured in many different ways. For example, the computing device 200 may be a conventional standalone computer or alternatively, the functions of computing device 200 may be distributed across multiple computer systems and architectures. The computing device 200 may be configured to perform some or all of the user behavior and business logic processing, or these functions may be distributed across multiple computer systems and architectures. In the embodiment shown in FIG. 1, the computing device 200 is linked, via network 150 or local network 124 (also described in FIG. 1), to other servers or systems housed by the hazard monitoring system 108, such as the load balancing server 114, and the application servers 112, and to the telematic monitoring system 130.

The computing device 200 may be configured in a distributed architecture, wherein databases and processors are housed in separate units or locations. The computing device 200 may also be implemented as a server located either on site near the hazard monitoring system 108, or it may be accessed remotely by the hazard monitoring company system 108. Some such units perform primary processing functions and contain at a minimum a general controller or a processor 202 and a system memory 208. In such an embodiment, each of these units is attached via the network interface unit 204 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 202 comprises a processor, such as one or more conventional microprocessors and one or more supplementary co-processors such as math co-processors for offloading workload from the CPU 202. The CPU 202 is in communication with the network interface unit 204 and the input/output controller 206, through which the CPU 202 communicates with other devices such as other servers, user terminals, or devices. The network interface unit 204 and/or the input/output controller 206 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 202 is also in communication with the data storage device 214. The data storage device 214 may comprise an appropriate combination of magnetic, optical and/or semiconductor memory, and may include, for example, RAM, ROM, flash drive, an optical disc such as a compact disc and/or a hard disk or drive. The CPU 202 and the data storage device 214 each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 202 may be connected to the data storage device 214 via the network interface unit 204.

The CPU 202 may be configured to perform one or more particular processing functions. For example, the computing device 200 may be configured for calculating hazard ratings related to user behavior. The same computing device 200 or another similar computing device may be configured for calculating a hazard risk for a user in a vehicle or local environment based at least upon one user behavior.

The data storage device 214 may store, for example, (i) an operating system 216 for the computing device 200; (ii) one or more applications 218 (e.g., computer program code and/or a computer program product) adapted to direct the CPU 202 in accordance with the present invention, and particularly in accordance with the processes described in detail with regard to the CPU 202; and/or (iii) database(s) 220 adapted to store information that may be utilized to store information required by the program. The database(s) 220 may include all or a subset of data stored in database 116, described above with respect to FIG. 1, as well as additional data, such as formulas or manual adjustments, used in establishing the hazard risk analysis for a user in a vehicle or other structure.

The operating system 216 and/or applications 218 may be stored, for example, in a compressed, an uncompiled and/or an encrypted format, and may include computer program code. The instructions of the program may be read into a main memory of the processor from a computer-readable medium other than the data storage device 214, such as from the ROM 212 or from the RAM 210. While execution of sequences of instructions in the program causes the CPU 202 to perform the process steps described herein, hardwired circuitry may be used in place of, or in combination with, software instructions for implementation of the processes of the present invention. Thus, embodiments of the present invention are not limited to any specific combination of hardware and software.

Figure 5:
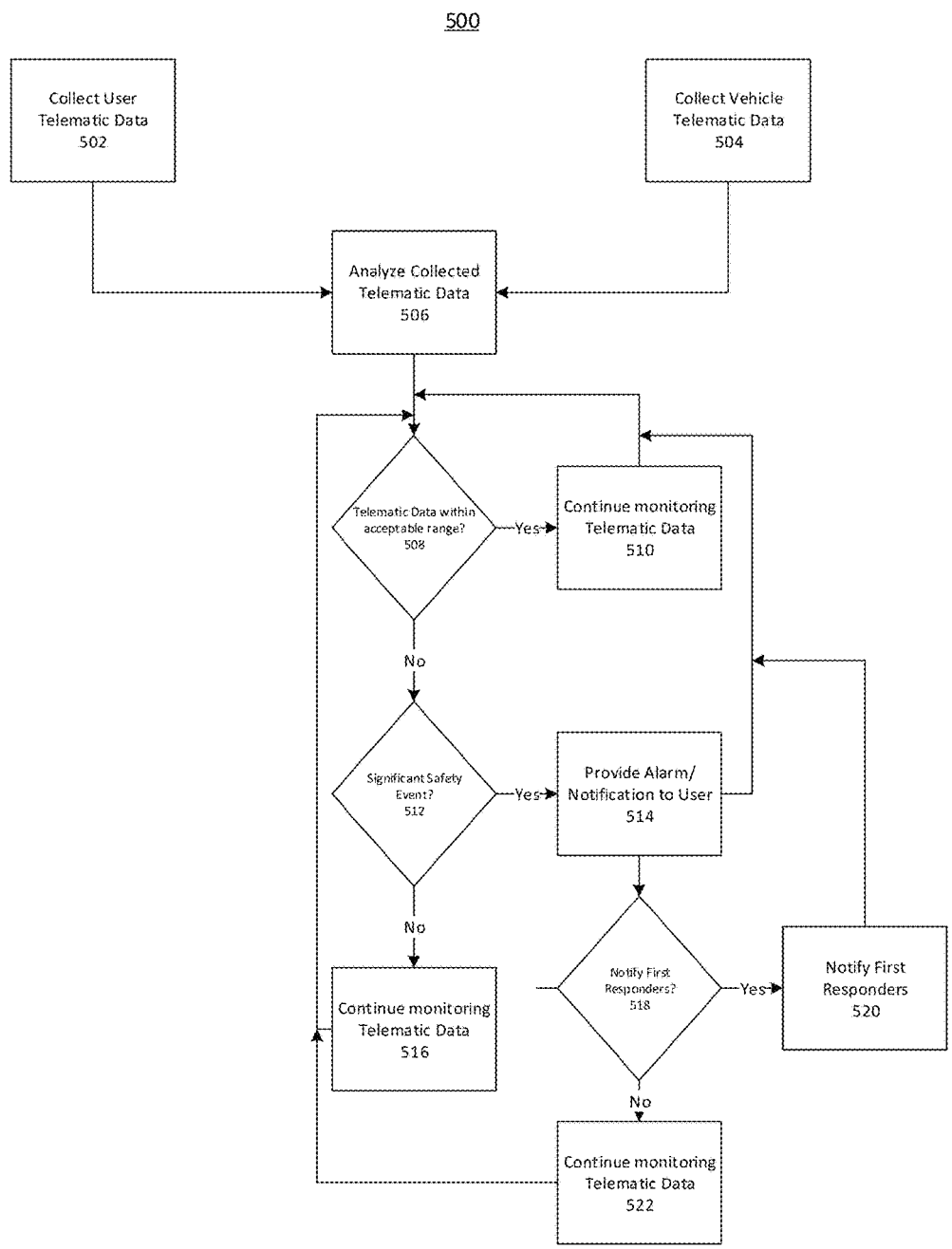
FIG. 5 is a flowchart of a method for determining user telematics data, according to an illustrative embodiment of the invention.
Figure 6:
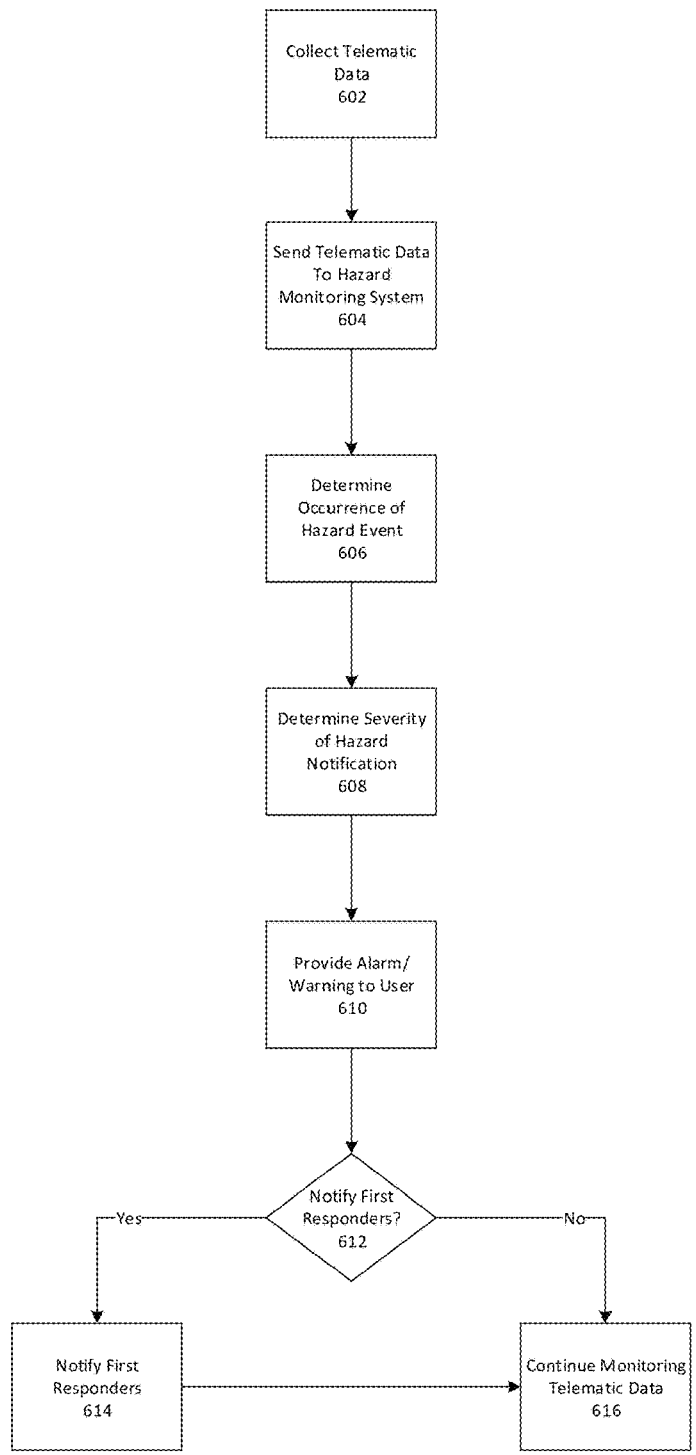
FIG. 6 is a flowchart of a method for determining user telematics data, according to an illustrative embodiment of the invention.

Suitable computer program code may be provided for analyzing user behavior and determining a hazard risk as described in relation to FIGS. 5 through 7. The program also may include program elements such as an operating system, a database management system and "device drivers" that allow the processor to interface with computer peripheral devices (e.g., a video display, a keyboard, a computer mouse, etc.) via the input/output controller 206.

The term "computer-readable medium" as used herein refers to any non-transitory medium that provides or participates in providing instructions to the processor of the computing device (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 202 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 3:
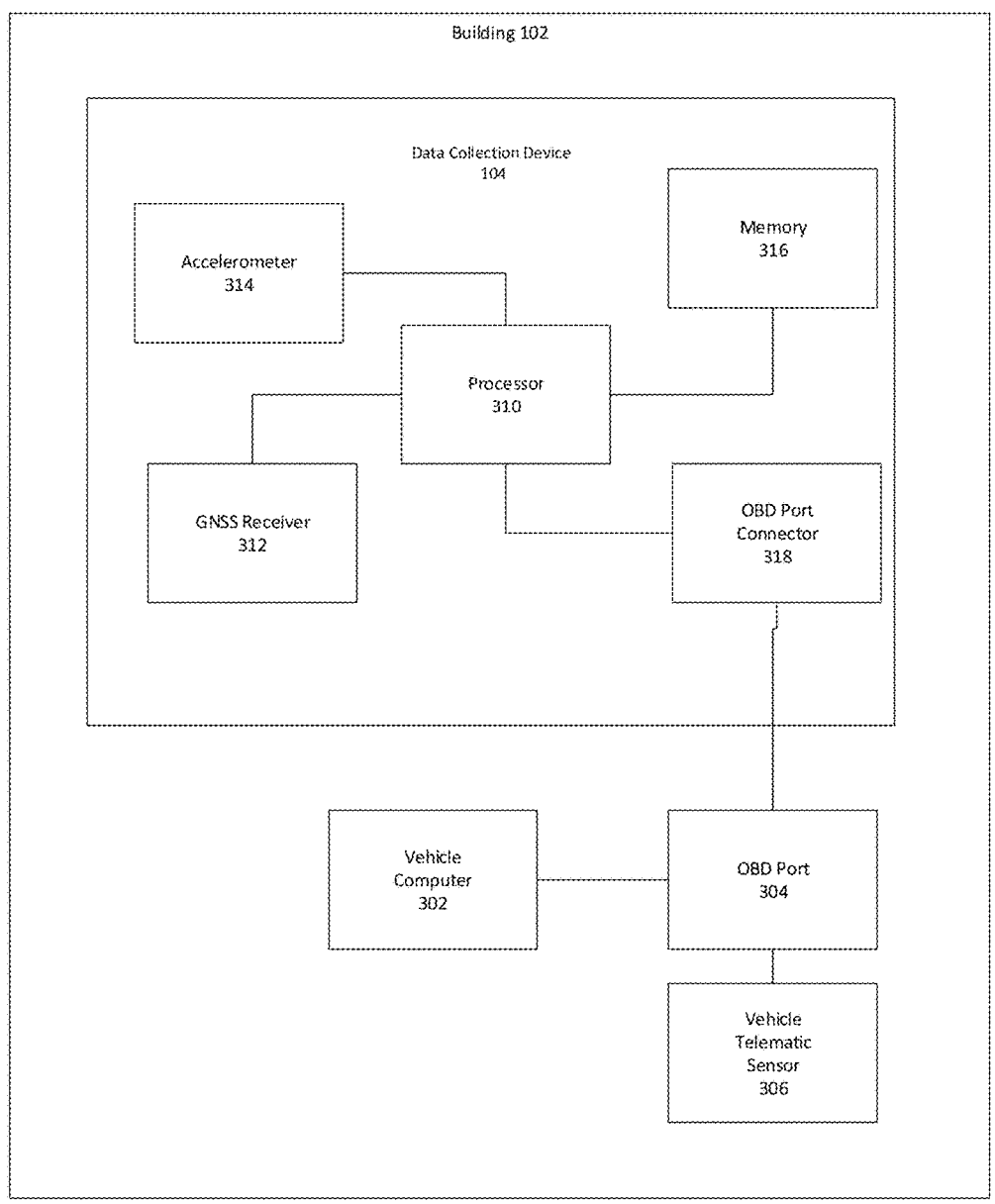
FIG. 3 is a block diagram of a vehicle environment and a device coupled to the vehicle for collecting telematic data and environmental data, according to an illustrative embodiment of the invention.

FIG. 3 is a block diagram of a vehicle 102 having a vehicle data collection device 104. As described in relation to FIG. 1, the vehicle 102 may be any automobile, motorcycle, truck, bus, watercraft, aircraft, or any other vehicle operated by a driver. The vehicle 102 includes a vehicle computer 302, a diagnostics (OBD) port 304, and vehicle telematics sensors 306. The vehicle data collection device 104 is connected to the vehicle 102 via an OBD port connector 318 connected to the OBD port 304 to receive telematics data and other information. The vehicle data collection device 104 includes a processor 310, a GNSS receiver 312, an accelerometer 314, and memory 316. The processor 310 can be a CPU, a microprocessor, an FPGA, or any other processing unit that can be configured to execute a software or firmware program for telematics data acquisition. The processor 310 is in communication with the other elements of the vehicle data collection device 104 to facilitate the operations of the vehicle data collection device 104. The processor can also be configured to process data received from the GNSS receiver 312, the accelerometer 314, and the OBD port connector 318. Data processing may include analyzing user behavior, determining if service is needed, determining if there is an unsafe status with the vehicle, formatting data, or encrypting data.

The GNSS receiver 312 includes an antenna and associated signal processing circuitry for receiving signals from global navigation satellite system (GNSS) satellites, such as the satellites numbered 1 through n in FIG. 1, and determining its location from the signals. GNSS satellites may be, for example, GPS, GLONASS, Galileo, or Beidou satellites which send time and orbital data from which the vehicle data collection device 104 can calculate its location. In some configurations, the processor 310 calculates the location of the user from data from the receiver 312. The processor 310 can pull location data from the GNSS receiver 312 at set time intervals, such as every 0.1 seconds, 0.2 seconds, 0.5 seconds, 1 second, 2 seconds, 5 seconds, or 10 seconds. The processor 310 sends the location data to the memory 316 along with a time and date stamp indicating when the user was at the location. In some embodiments, the GNSS receiver 312 may be part of a separate GNSS device used by the user for obtaining user directions. In this case, the GNSS receiver 312 transmits data to the user data collection device 128 and/or vehicle data collection device 104 though a wired connection or a wireless connection, e.g., BLUETOOTH or Wi-Fi.

The accelerometer 314 is a device that measures proper acceleration related activity. Data collected from an accelerometer 314 may include or be used for obtaining safety events or condition of the vehicle. Some or all of these types of data are received or calculated by the processor 310. The processor 310 may collect data at intervals such as every 0.1 seconds, 0.2 seconds, 0.5 seconds, 1 second, 2 seconds, 5 seconds, or 10 seconds and store the data in the memory 316. Each data point is time and date stamped and/or location stamped. In some embodiments, the processor 310 determines intervals between data stored in the memory 316 based on trends in the data.

The OBD port connector 318 is used to collect data from the vehicle computer 302 and/or vehicle telematics sensors 306 via OBD port 304. The OBD port 304 can have a standard interface, such as OBD-I, OBD-1.5, OBD-II, EBD, EBD2, JBD, ADR 79/01, or ADR 79/02. Instead of an OBD port 304, any other port and corresponding connector for receiving data from a vehicle's computer can be used. The vehicle computer 302 may provide information about the vehicle's diagnostics. Vehicle diagnostics data can be used to determine the presence of any vehicle malfunctions, such as poor air quality, seismic events, structural integrity issues, high temperature, loss of electrical power, or fire conditions. With the vehicle diagnostics data, it is possible to determine whether a safety event was caused by the user's actions or related to the malfunction, and thus not reflective of the user's user habits. The vehicle may contain additional telematics sensors 306 for, e.g., vehicle tracking, monitoring electrical consumption, and vehicle safety. Data obtained by the vehicle data collection device 104 from the vehicle computer 302 and telematics sensors 306 via the BD port 304 can supplement or be used instead of data collected by the GNSS receiver 312 and/or accelerometer 314. In some embodiments, the vehicle data collection device 104 turns on automatically when the vehicle 102 is with power, and the vehicle 102 may power the vehicle data collection device 104.

In some embodiments, the vehicle data collection device 104 may also be configured to communicate with the user via an external user interface, such as a display screen within the vehicle 102. The external user interface includes output components, such as a screen or speakers, and may include input components, such as a touch screen, keyboard, or microphone. The external user interface can output user behavior data, vehicle diagnostics data, a service alert, a malfunction alert, and any data collected from the GNSS receiver 312, accelerometer 314, and/or BD port 304.

In some embodiments, rather than running the data acquisition program on a dedicated data acquisition device installed in the vehicle, the data acquisition program runs on the user's mobile device, such as an IPHONE™, BLACKBERRY™, or any other smartphone or mobile computing device configured to collect data that can be used to analyze user behavior and/or vehicle status. The data can be collected using sensors, such as a GNSS receiver or accelerometers, in the mobile device, or the data can be transmitted from the vehicle and received by the mobile device via a wired or wireless connection.

Figure 4:
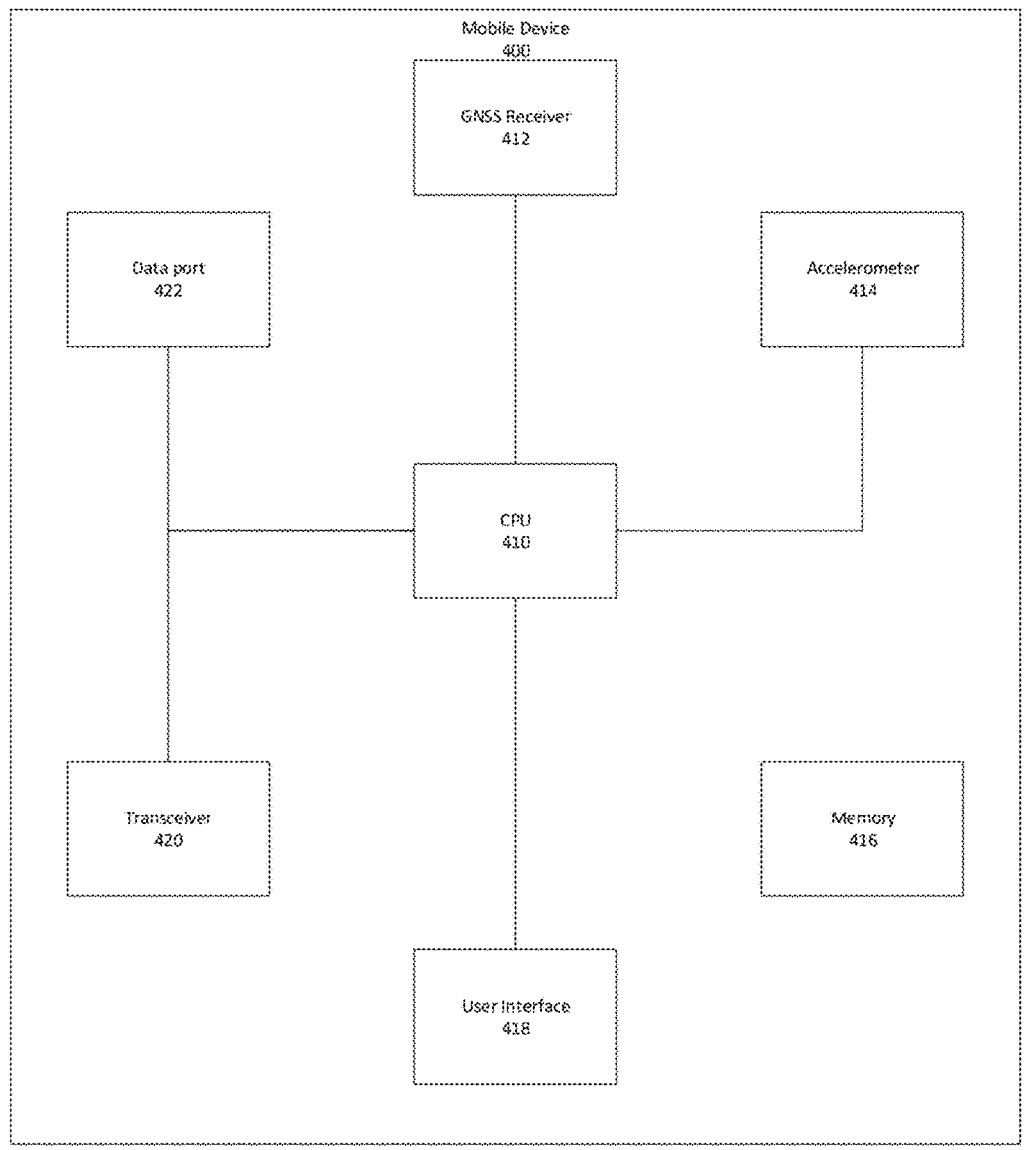
FIG. 4 is a block diagram of a mobile device used within a vehicle for collecting data according to an illustrative embodiment of the invention.

FIG. 4 is a block diagram of an exemplary mobile device 400 that can be used instead of the vehicle data collection device 104. The mobile device 400 includes a CPU 410, a GNSS receiver 412, a accelerometer 414, and a memory 416, which are similar to the processor 310, the GNSS receiver 312, the accelerometer 314, and the memory 316, respectively, described above in relation to FIG. 3. The mobile device 400 also includes a user interface 418, a transceiver 420, and a dataport 422. The CPU 410 is configured to execute a software application for telematics data acquisition. The CPU 410 is in communication with all of the other elements of the mobile device 400 to facilitate the operation of the data collection device 400, and can perform processing similar to the processing performed by the processor 310 described above in relation to FIG. 3.

A user of the mobile device interacts with the mobile device through the user interface 418. The user interface 418 can include one or more of a screen, a touch screen, a speaker, a headphone jack, a keyboard, and a microphone. One or more transceivers 420 are used to connect to and exchange data over a cellular network, the Internet, a BLUETOOTH™ connection, or other wireless communications pathways. The dataport 422 is used for wired communication with the vehicle and/or the telematic monitoring system 130. The data acquisition application can be downloaded from the network or the telematic monitoring system 130 either wirelessly using the transceiver 420 or through a wired connection using the dataport 422. Once the data acquisition application has been installed, it should be executed each time the user 110 enters the vehicle. The user can use the user interface 418 to execute the data acquisition application each time he enters the vehicle. In some embodiments, the mobile device 400 can automatically execute the data acquisition application when the mobile device 400 determines that it is in a vehicle by processing the signals from the GNSS receivers 412 and/or other methods.

In some embodiments, the mobile device 400 is connected to the vehicle by a wireless connection (e.g., BLUETOOTH) or a wired connection using the transceiver 420 or the dataport 422, respectively. In such embodiments, the mobile device 400 can be configured to automatically execute the data acquisition application based on the presence of the vehicle connection. While in the vehicle, the vehicle's computer can send telematics data to the mobile device 400. If the mobile device 400 receives data indicating a vehicle malfunction/safety event, the CPU 410 can create an alert, and the alert can be communicated to the user via the user interface 418. Telematics data received from the vehicle and/or detected by the GNSS receivers 412 or accelerometers 414 is stored in memory 416. The telematics data can be sent to the telematic monitoring system 130, vehicle data collection device 104, and/or data processing service 106 in real time, near-real time, or after a longer period of data collection via the transceiver 420, or the data can be transmitted after a period of data collection via the data port 422.

FIG. 5 is a flowchart of a method for providing a warning/alarm based on collected user telematic data and vehicle telematic data 500. User telematic data and vehicle telematic data are collected (steps 502 and 504) or after being collected, the user data collection device 128, vehicle data collection device 104 or a mobile device 400 transmits the user telematic data and/or building telematic data to the monitoring system where the data is analyzed (step 506). The data is analyzed and compared against a standard indicating for each the data type. Subsequently, a determination is made if the user 110 is operating or otherwise functioning in a condition or environment that is within or outside acceptable ranges (determination 508) for that type of activity.

For activities where the user 110 is operating within acceptable parameters, the system continues to monitor the telematic data (step 510). For activities where the user 110 is operating outside of acceptable parameters, initially the system makes a determination as to the severity of activity (determination 512). Based upon the severity of the event, the system may continue to monitor the telematic data (step 516), and/or it may determine to provide an alarm/notification to the user (step 514). Alternatively or additionally, notification may be made to a health care provider (determination 518, step 520) and/or first responders such as, without limitation, police, firemen, paramedics, etc. Again, the system may continue monitoring the telematic data (step 522).

The resulting data may be stored and maintained at the hazard monitoring company. As discussed, the data may be used to determine modifications to hazard parameters or otherwise as needed.

FIG. 6 describes a method for determining a hazard alarm/notification occurrence for a user based on telematics data once the telematics data acquisition program has been installed. The telematics data acquisition program on the vehicle data collection device 104 or mobile device 400 collects data related to the user's behavior and the condition of the vehicle/vehicle environment, as described in relation to FIGS. 3 and 4 (step 602), during a data acquisition period or monitoring period. The user 110 can be monitored for any period of time over which a sufficient amount of data to analyze the user's user behavior can be collected, e.g., 1 minute, 1 hour, 1 day, 1 month, 2 months, 3 months, or 6 months.

As the data is being collected or after the data has been collected, the vehicle data collection device 104 or mobile device 400 transmits the data to the hazard monitoring system 108 (step 604). As previously mentioned, the data may be processed by the telematic monitoring system 130 and/or a third party data processing service 106 before being sent to the hazard monitoring system 108. The hazard monitoring system 108 then determines an alarm/notification status (step 606) based on the received telematics data as well as data related to the vehicle and the user 110. Determining the alarm/notification status is described in further detail in relation to FIG. 7.

Once the alarm/notification status has been determined, the hazard monitoring system 108 transmits the alarm/notification to the user 110 for his/her consideration (step 610). The alarm/notification may include several possible types of different information from which the user 110 can review.

The user 110 then determines whether to act on the information (step 612). If the user 110 follows the alarm/notification, the hazard monitoring company documents the user 110 action (step 614). If the user 110 declines to follow the alarm/notification, the hazard monitoring company may provide periodic reminder alarm/notifications of a continued hazard (step 616).

FIG. 7 provides greater detail into the factors involved in developing a hazard alarm/notification. The hazard alarm/ notification is derived from four main classes of data: vehicle data 710, user data 720, user telematic data 770, and vehicle telematics data 730. The vehicle telematics data 730 is processed to generate data related to user behavior and vehicle/vehicle environmental conditions. Based on the vehicle condition, a malfunction/safety alert may be provided to the user 110. In addition to the vehicle data 710, user data 720, user telematic data 770, and vehicle telematics data 730, data from previous telematics monitoring 762 and service history data 760 can be used to determine the hazard alarm/notification 780. The processing steps for processing the data described in relation to FIG. 7 and determining a hazard alarm/notification event can be performed at the hazard monitoring system 108, the third party data processing service 106, the telematic monitoring system 130, the vehicle data collection device 104 or mobile device 400, or any combination of these systems and devices.

Vehicle data 710 is comprised of data relating to the vehicle. The vehicle data 710 includes construction materials, vehicle location, nature of vehicle use (commercial, industrial, etc.), age of vehicle, etc. If the vehicle has special feature, this data is also included in the vehicle data 710. The vehicle data 710 also includes the age of the vehicle 714, the mileage of the vehicle 715, and the history of the vehicle 716. The history 716 includes information on any events, such as accidents or safety events, of the vehicle or those in the area. The history 716 also includes any available service records and any available information related to how the vehicle was used by its previous owner(s). The vehicle data may also include the purchase price and/or resale price of the vehicle.

User data 720 is comprised of the data associated with the user 110. The user data 720 includes basic contact information 721 of the user 110, including the user's name, address, telephone number(s), fax number, email address, etc. The user data 720 also includes basic demographic data, such as gender 722 and age 723. The user data 720 also includes data that can be used to analyze the user's finances and financial responsibility, such as social security number 724 and employment information 725. The user data 720 also includes the user's medical history 726, with which the hazard monitoring company 108 can retrieve information on the user's user history.

The user telematics data 770 includes data collected by the data acquisition program. The user telematic data includes sensed data about the user's health and overall condition such as, blood pressure, body temperature, perspiration, body mass index, blood glucose level, blood alcohol content, brain function, activity level, respiratory rate, eye dilatation, etc. Additionally or alternatively, the user telematic data 770 includes sensed data about the user's environment. Such data includes, but is not limited to, oxygen content, carbon monoxide level, methane gas detection, hydrogen sulfide gas (or any dangerous or poisonous fluid) presence, etc. The user telematic data 770 is generally a measure of any environmental factor such as weather, road conditions, daylight etc. the user is experiencing during or around vehicle operation.

The vehicle telematics data 730 includes data collected by the data acquisition program. The vehicle telematics data 730 includes GNSS data 731 and accelerometer data 732 collected by the GNSS receivers 312 or 412 and accelerometers 314 or 414, respectively. The telematics data also includes data collected from the OBD port, such as energy usage data 733, safety event deployment data 734, and HVAC diagnostics data 735. The telematics data 730, particularly the GNSS data 731, accelerometer data 732, and any data received from the vehicle computer relating to safety events (e.g., fire event, carbon dioxide event, etc.) are processed to generate metrics indicative of user behavior.

The vehicle telematics data 730 is also analyzed to determine whether the vehicle is malfunctioning or has experienced a safety event (decisions 750 and 752). The vehicle diagnostics data 735, the airbag data 734, and data indicating the misuse are particularly relevant for these determinations. If the vehicle is malfunctioning or has experienced a safety event, an alert (754 or 756) is generated and communicated to the user's telephone, smart phone, computer, or any other communications device, or to the vehicle 102. The alert can be in the form of a phone call, a voice mail, a text message, an email, an alert on the vehicle's dashboard, or any other type of communication. The alert can include the type of safety event or a description of the malfunction, a level of urgency of reacting to the safety event or possible courses of action.

In some embodiments, the user 110 may have telematics data 762 from previous telematics monitoring that was performed by the same hazard monitoring company, a different hazard monitoring company, or not associated with a hazard monitoring company. The previous telematics data 762 may be similar to the telematics data 730. If the hazard monitoring system 108 can access the previous telematics data 762, it can use this to generate a hazard alarm/notification without collecting telematics data 730. In this case, an alarm/notification can be generated as soon as the previous telematics data 762 is available to the hazard monitoring system 108. In other embodiments, telematics data 730 is still gathered, and it is supplemented by the previous telematics data 762. If the telematics data 762 was collected by a different hazard monitoring company or a different vehicle data collection device 104, the format of the data may not be in the format used by the hazard monitoring system 108 for calculating a hazard alarm/notification. In this case, the hazard monitoring system 108 can convert the data format into the data format output by the hazard monitoring company's data acquisition program.

In some embodiments, data from a third party data provider 764 is also accessed for generating the hazard alarm/notification. For example, data from a third party data provider 132 may provide additional information related to the user 110, such as the user's safety record or medical history. Other third party data, such as injury accidents and weather data, is processed in conjunction with the received telematics data to evaluate user patterns in view of the vehicle conditions, and may be used when evaluating the user.

Based on some or all of the vehicle data 710, user 110 data 720, user telematic data 770, vehicle telematics data 730, processed user behavior characteristics 740-748, service history 760, previous telematics data 762, third party data 764, and current health data 770, the hazard monitoring system 108 determines a hazard alarm/notification event for the user. Safe user behaviors, user health factors within tolerance, user environmental factors within tolerance, good vehicle conditions, and good medical history may be associated with higher hazard event tolerance. The various factors may be rated separately, e.g., an overall safety rating can be calculated, or a user behavior rating can be calculated. The factors can be weighted and the hazard alarm/notification event based on the various rating factors and their relative weights. In some embodiments, the hazard monitoring system 108 uses the telematics data 730 in an algorithm for generating a hazard alarm/notification event.

An aspect of the disclosure includes a system for processing environmental safety status, health data, and vehicle data related to a hazard alarm/notification for a user 110. The system comprising a communications interface configured to receive user health telematics data collected by a telematics data acquisition device. The telematics data acquisition device is configured to collect user health telematic data of a user safety status. The user health telematic data being indicative of the user safety status while operating a vehicle. The system is configured to receive vehicle telematic data collected by a telematics data acquisition device. The telematics data acquisition device is configured to collect telematics data of a vehicle. The telematics data is indicative of the safety of the vehicle while being operated by a user. The system is configured to provide the health telematic and the vehicle telematic data to a business logic processor for the development of a hazard alarm/notification based on at least one of the received health telematics data or vehicle telematic data. The system is configured to transmit the hazard alarm/notification to the user.

A further aspect includes a hazard alarm/notification system disclosed includes the user health telematics data collected by a telematics data acquisition device. The data contains telematic data that is at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

A further aspect includes a hazard alarm/notification system wherein health telematics data indicates an unsafe condition for the user.

Yet another aspect includes a hazard alarm/notification system wherein the telematics data indicative of safety of the vehicle includes telematic data that is at least one of a vehicle speed, vehicle handling, driving times, distance traveled, location of the vehicle, and condition of the vehicle.

A further aspect includes a hazard alarm/notification system wherein vehicle telematics data indicates an unsafe condition for the user.

Another aspect includes a hazard alarm/notification system further comprising transmitting the hazard alarm/notification to a first responder, such as, a policeman, a fireman, or a paramedic.

A still further aspect includes one or more tangible computer readable media storing computer readable instructions that, when executed, perform a method of providing a hazard alarm/notification to a user based upon human health telematic data and vehicle telematic data, including receiving health telematic data via a communications interface health telematics data collected by a telematics data acquisition device. Also, receiving vehicle telematic data via a communications interface vehicle telematics data collected by a telematics data acquisition device. This includes determining a hazard alarm/notification based on the received health telematic data and the received vehicle telematic data. Also included is transmitting the hazard alarm/notification to the user.

The computer readable media includes the step of receiving health telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

Also included is the computer readable media wherein the health telematic data indicates the user is in an unsafe condition.

Additionally included is the computer readable media wherein the step of receiving vehicle telematic data includes receiving vehicle telematic data of at least one of a vehicle speed, vehicle handling, driving times, distance traveled, location of the vehicle, and condition of the vehicle.

The computer readable media wherein the vehicle telematic data indicates the user is in or near an unsafe environment or location.

Also included is the computer readable media wherein the step of transmitting the hazard alarm/notification to the user includes transmitting the hazard alarm/notification based upon an unsafe condition detected with the user's health.

Further, the computer readable media wherein the unsafe condition detected with the user's health is related to user telematic data. This includes data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

An additional aspect includes the computer readable media wherein the step of transmitting the hazard alarm/notification to the user includes transmitting the hazard alarm/notification based upon an unsafe condition detected with environmental conditions in the user's location.

Also includes is the computer readable media wherein the vehicle conditions include at least one of a vehicle speed, vehicle handling, driving times, distance traveled, location of the vehicle, and condition of the vehicle.

Yet another non limiting aspect of this disclosure includes a sensor system that has a first sensor, to be worn by a user. The first sensor outputting a first sensor data indicative of measured at least one user health telematic data. Additionally included is a second sensor, in communication with a vehicle being operated by the user, the second sensor outputting a second sensor data indicative of a measured at least one vehicle telematic data. Also, a computing unit, in communication with the first sensor and the second sensor. The computing unit storing program instructions for execution by the computing unit to, receive the first sensor data and the second sensor data, calculate a risk level associated with the first sensor data and the second sensor data, and, output a hazard alarm/notification feedback signal to the user indicative of the risk level of the first sensor data and the second sensor data.

Also included is a sensor system wherein the first sensor data is user telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

Also included is a sensor system wherein the output signal to the user is a hazard alarm/notification indicative of the user telematic data indicating the user spending excessive time in an area having a predetermined dangerous or unsafe level or condition.

Another aspect includes a sensor system further including providing a hazard alarm/notification output feedback signal to the hazard alarm/notification to a first responder, such as, a policeman, a fireman, or a paramedic.

Yet another aspect includes a sensor system wherein the second sensor data is data related to at least one of a vehicle speed, vehicle handling, driving times, distance traveled, location of the vehicle, and condition of the vehicle.

Also, a sensor system further includes providing a hazard alarm/notification output feedback signal to a first responder, such as, a policeman, a fireman, or a paramedic.

Another aspect of the disclosure is a method for providing a hazard alarm/notification based upon human health telematic data and vehicle telematic data. The method comprising, receiving, by a communications interface, user health telematics data collected by a telematics data acquisition device. The user health telematics data being indicative of a user health status health while operating a vehicle. Also, receiving, by a communications interface, vehicle telematic data collected by a telematics data acquisition device, the vehicle telematics data being indicative of a vehicle safety status health while being operated by a user. Further, determining, by the business logic processor, a hazard alarm/notification for the user based on the received user health telematic data and vehicle telematic data. Additionally, providing by the business logic processor the hazard alarm/notification to the communications interface. Also, transmitting, by the communications interface, the hazard alarm/notification to the user.

The method further comprising transmitting, by the communications interface, the hazard alarm/notification to a first responder, such as, a policeman, a fireman, or a paramedic.

A further aspect of the disclosure is a method of providing human telematic based hazard alarm/notification to a user based upon human telematic data and vehicle telematic data. The additional aspect comprising providing a first sensor, to be worn by a user, a first sensor data indicative of measured at least one user health telematic data. Also, providing a second sensor, in communication with a vehicle being operated by the user, the second sensor outputting a second sensor data indicative of a measured at least one vehicle telematic data. This aspect also includes providing a computing unit, in communication with the first sensor and the second sensor, the computing unit storing program instructions for execution by the computing unit. The computing unit receiving the first sensor data and the second sensor data and calculating a risk level associated with the first sensor data and the second sensor data. The computing unit is also providing a hazard alarm/notification output feedback signal indicative of the risk level of first sensor data and the second sensor data to the user.

The method further comprising transmitting, by the communications interface, the hazard alarm/notification to a first responder, such as, a policeman, a fireman, or a paramedic.

An additional aspect includes a method wherein the user health telematic data is user telematic data about at least one of a body mass index, blood pressure, respiratory rate, heart rate, perspiration, body temperature, eye dilation, blood sugar level, brain function (EEG), vacillations in blood sugar level, hours of sleep, physical activity rate and duration, water consumption, food consumption, alcohol consumption, amount of sunlight exposure, and/or exposure to any variety of air or water pollutants data.

Yet another aspect includes a method wherein the vehicle telematic data include at least one of a vehicle speed, vehicle handling, driving times, distance traveled, location of the vehicle, and condition of the vehicle.

While various embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for processing vehicle operator status data and vehicle data related to determination of a hazard alarm/notification for a user, the system comprising:
   a communications interface configured to:
   receive user health telematic data collected by a user health telematics data acquisition device, wherein the user health telematics data acquisition device is configured to collect user health telematic data via at least one telematic sensor worn by the user wherein the sensor has direct physical contact with the user, the user health telematic data being indicative of the user health status while operating a vehicle;
   accessing a historic vehicle telematic data collected by a vehicle telematic data acquisition device, wherein the vehicle telematic data acquisition device is configured to collect telematic data of the vehicle, the historic vehicle telematic data indicative of at least one historical attribute of the vehicle including a safety event deployment data indicating a prior vehicle collision event;
   receive environmental telematic data collected by an environmental telematic data acquisition device, the environmental telematic data being indicative of an environmental status around the user;
   provide the user health telematic, the historic vehicle telematic data, and the environmental telematic data to a business logic processor for the development of a hazard alarm/notification based on at least one of the received user health telematic data, historic vehicle telematic data, or environmental telematic data; and,
   transmit the hazard alarm/notification to the user via a mobile device.

2. The system of claim 1, wherein the user health telematic data collected by a telematic data acquisition device contains telematic data about at least one of a body mass index, blood pressure, respiratory rate, heart rate, perspiration, body temperature, blood sugar level, vacillations in blood sugar level, hours of sleep, physical activity rate and duration, water consumption, food consumption, alcohol consumption, amount of sunlight exposure, and/or exposure to any variety of air or water pollutants data.

3. The system of claim 2, wherein health telematic data indicates an unsafe condition for the user.

4. The system of claim 1, wherein the historic telematic data includes historic telematic data that is at least one of a vehicle purchase price, vehicle malfunction history, vehicle maintenance history, location of vehicle use, distance traveled, condition of the vehicle, and prior use of vehicle.

5. The system of claim 4, wherein historic telematic data indicates an unsafe condition for the user.

6. The system of claim 1, further comprising transmitting the hazard alarm/notification to a first responder, such as, a policeman, a fireman, or a paramedic.

7. The system of claim 1, wherein the environmental telematic data includes data indicative of a sensed quality or presence of at least one of an oxygen content level, carbon monoxide content level, methane content level, pollution content level, or radiation content level.

8. The system of claim 1, wherein the development of a hazard alarm/notification further includes using telematic data from prior telematic data monitoring.

9. The system of claim 1, wherein accessing the historic vehicle telematic data includes accessing history of airbag data.

10. The system of claim 1, wherein accessing the historic vehicle telematic data includes accessing history of safety deployment event data involving airbag deployment.

11. The system of claim 1, wherein accessing the historic vehicle telematic data includes accessing history of vehicle diagnosis data.

12. The system of claim 1, wherein accessing the historic vehicle telematic data includes accessing history of the vehicle's prior use.

13. The system of claim 1, further comprising, sensing a current vehicle telematic data wherein the current vehicle telematic data is indicative of at least one current vehicle telematic attribute of the vehicle.

14. The system of 13, wherein the current vehicle telematic data is at least one of a vehicle speed, vehicle location, vehicle drive time, and vehicle condition.

15. The system of claim 13, wherein the development of a hazard alarm/notification is also based on analysis of current vehicle telematic data.

\* \* \* \* \*